United States Patent [19]

Renirie

[11] 4,023,046
[45] May 10, 1977

[54] LOW CURRENT DRAIN AMPLIFIER INCORPORATING MEANS FOR MINIMIZING SENSITIVITY DRIFT

[75] Inventor: Alexis C. M. Renirie, Nijmegen, Netherlands

[73] Assignee: Vitatron Medical B.V., Dieren, Netherlands

[22] Filed: Aug. 28, 1975

[21] Appl. No.: 608,529

[52] U.S. Cl. .............................. 307/360; 307/230; 330/69

[51] Int. Cl.² .................................. H03K 5/20

[58] Field of Search .......... 330/69, 146; 307/235 F, 307/235 G, 235 H, 235 J, 235 N, 235 P, 235 T, 230

[56] References Cited
UNITED STATES PATENTS

| | | | |
|---|---|---|---|
| 3,639,824 | 2/1972 | Malavasi | 330/69 UX |
| 3,679,916 | 7/1972 | Siebers | 307/230 X |
| 3,792,367 | 2/1974 | Fleischer et al. | 330/98 |
| 3,805,091 | 4/1974 | Colin | 330/109 X |
| 3,851,259 | 11/1974 | Porawski | 307/235 N X |
| 3,924,199 | 12/1975 | Pearlman | 330/107 |

*Primary Examiner*—James B. Mullins
*Attorney, Agent, or Firm*—Woodcock Washburn Kurtz & Mackiewicz

[57] ABSTRACT

An amplifier circuit for detecting low level signals of positive or negative amplitude, and for producing an output pulse whenever the input signals exceed a predetermined threshold level. The threshold level, or sensitivity of the amplifier circuit, is established through use of a pair of operational transconductance amplifiers employed as comparators, the reference voltage for each comparator being set through a resistive circuit driven by one or more current sources. The design provides for compensation of amplifier offsets with minimal adjustment requirements, and permits operation with very low current drain.

15 Claims, 7 Drawing Figures

LOW CURRENT DRAIN AMPLIFIER INCORPORATING MEANS FOR MINIMIZING SENSITIVITY DRIFT

BACKGROUND OF THE INVENTION

1. Field of the Invention

This invention lies in the field of electronic amplifiers and, more particularly, amplifiers suitable for low signal threshold amplification with low current drain operation.

2. Description of the Prior Art

There are a wide variety of present day applications which require amplification of low level signals under extremely low current drain, or low power consumption conditions. For example, in the field of implantable electronic pacers for cardiac pacing, where the battery energy of an implanted pacer must be conserved to the maximum extent possible, there exists an acute need for an amplifier which is capable of detecting when low level incoming signals exceed a predetermined threshold and amplifying same so as to produce a resultant output pulse, under circuit conditions which require a minimum current drain from the pacer battery. More particularly, in demand-type pacers where output stimulus pulses are delivered only in the absence of natural pulses, the quiescent current drain from the battery is determined largely by the design of the amplifier portion which recognizes and amplifies the incoming natural beats and generates an output signal suitable for resetting of the pacer oscillator. For further background on this problem, reference is made to the co-pending application titled "Multiple Function Demand Pacer With Low Current Drain," filed concurrently herewith and assigned to the same assignee.

It has long been considered virtually impossible to design an amplifier suitable for use in an implanted pacer which would draw only on the order of 1 micro-amp, but this has remained a standard which the industry has hoped to achieve. At the same time, any successful amplifier design must provide that the characteristics will be essentially the same in the environment where the amplifier is to be used as they are when they are tested. In the specific example of electronic pacers, one of the critical requirements is that the drift in threshold level, or sensitivity, from the temperature at which tested as compared to the operational temperature of about 37° C, be minimized to the greatest possible extent. Also, to insure uniformity of amplifier characteristics for production devices, it is desired that the amplifier design provide maximum independence of the normal variation in components, so as to avoid the increased expense of utilizing extremely low tolerance elements or difficult adjustment procedures.

SUMMARY OF THE INVENTION

It is an object of this invention to provide an amplifier circuit having the capability of detecting input signals of only several millivolts (mV) and for producing an output signal of desired magnitude and waveform corresponding to input signals above a predetermined threshold, while simultaneously blocking lower level signals, all while maintaining quiescent current drain as low as possible.

It is a further object of this invention to provide an amplifier circuit for providing high gain amplification of input signals above a predetermined threshold level, the circuit being substantially insensitive to variations of the power supply and being relatively easy to adjust for accurate threshold detection.

It is another object of this invention to provide an amplifier circuit for providing a predetermined output drive signal upon receiving an input signal of either positive or negative polarity which exceeds a predetermined threshold level, which amplifier operates with a current drain of only about 1 micro-ampere (1 uA), which is substantially independent of circuit component variations and the condition of the power supply, has minimal drift in operating characteristics as a function of temperature, and is simple to adjust in order to obtain the desired threshold characteristics.

In accordance with the above objectives, there is provided an amplifier circuit having a first amplifier stage including an operational transconductance amplifier (OTA) and a comparater stage comprising a pair of operational transconductance amplifiers connected in inverting and non-inverting modes and being operated with a bias or reference voltage across their differential inputs which, together with the amplifier stage, establishes the desired sensitivity. In order to precisely establish the desired threshold and to compensate for the offset inherent in each operational transconductance amplifier, means are provided including a current source in combination with a predetermined resistive network for establishing desired bias voltages at the comparator amplifiers. The threshold establishing, or sensitivity circuits, are designed to maximize ease of the adjustment procedure for establishing the sensitivity, and to minimize drift in the sensitivity characteristics as a function of the ambient operating temperature.

CROSS-REFERENCE TO RELATED APPLICATIONS

The following applications are filed concurrently herewith, are assigned to the same assignee, and are incorporated by reference:

1. MULTIPLE-FUNCTION DEMAND PACER WITH LOW CURRENT DRAIN Invention of Alexis C. M. Renirie Ser. No. 608,465, filed Aug. 28, 1975.

2. LOW CURRENT DRAIN AMPLIFIER WITH SENSITIVITY ADJUSTMENT MEANS, Invention of Alexis C. M. Renirie, and Godefridus J. M. Weijs Ser. No. 608,587, filed Aug. 28, 1975.

3. LOW CURRENT DRAIN AMPLIFIER INCORPORATING FEEDBACK MEANS FOR ESTABLISHING SENSITIVITY, Invention of Alexis C. M. Renirie, Godefridus J. M. Weijs and Jan P. Schuimer Ser. No. 608,588, filed Aug. 28, 1975.

DESCRIPTION OF THE PREFERRED EMBODIMENT

Figure 1:
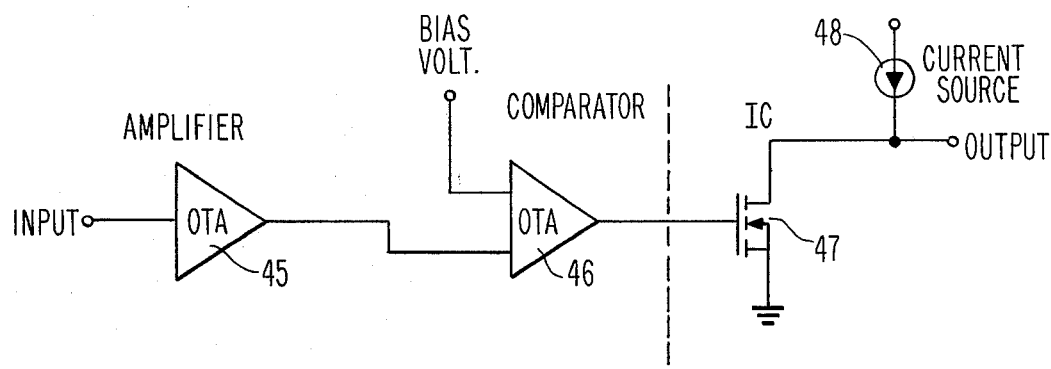
FIG. 1 is a diagrammatic drawing of the basic components of the amplifier circuit of this invention.

Referring now to FIG. 1, there is shown the basic configuration around which the various embodiments of the amplifier circuit of this invention are constructed. As shown, there is a first operational transconductance amplifier (OTA) 45 which operates basically as an amplifier stage. The OTA acts as a current source at its output, providing an output current which is proportional to the differential input voltage placed across its two input terminals. The polarity of the output current is dependent upon the polarity of the differential input voltage. The OTA has a special bias current terminal for receiving bias current $I_{ABC}$, which bias current determines the essential characteristics of the OTA, and particularly the transconductance and the current drain. The total current drain of an OTA, including $I_{ABC}$, is $3 \times I_{ABC}$, such that the current drain of the device can be established by fixing $I_{ABC}$. A suitable operational transconductance amplifier for use in this invention is the RCA linear integrated circuit CA3080. Reference is made to the RCA literature for a full description of the characteristics of this device. Reference is also made to the RCA application note ICAN-6668, dated November 1973, which notes provide material explanatory of the circuit characteristics of the operational transconductance amplifier. As used in claiming this invention, the output of the first stage OTA is direct connected to a second stage OTA 46 which is utilized as a comparator device. Of the two input terminals of the second stage OTA, one receives the output of the first stage amplifier, in either an inverting or non-inverting mode, and the other input terminal receives a bias voltage, the quiescent voltage difference across the two terminals establishing the magnitude of input swing required to cause a change in polarity of the output signal from the OTA comparator. Thus, if the amplitude of the signal coming from the amplifier OTA is larger than a fixed reference level established across the differential inputs of the comparator OTA, and opposite in polarity, the input voltage of the comparator OTA changes from one polarity to another, thus switching the comparator output signal. In practice, the voltage gain of the amplifier stage is generally between 10 and 20, which gain is one of the determinants of the swing in the input level to the first amplifier stage which is required to switch the output of the comparator.

Still referring to FIG. 1, the output of comparator 46 is direct coupled into the gate of the CMOS transistor 47, which as shown has its source connected to ground and its drain connected to a current source 48. Because the OTA is a current source itself, and the input resistance of a CMOS transistor is extremely high, the voltage gain of the comparator OTA is very high. For example, for a transconductance of 2 uA/V and an internal resistance of $75 \times 10^9$ ohms, the gain is 150,000. This extremely high gain provides a very high switching response, such that as soon as the input to OTA 45 exceeds a predetermined signal threshold, the output of comparator 46 switches essentially instantly from a negative to a positive current, thus driving transistor 47 conductive and producing a voltage change at the output terminal suitable for driving the output load connected thereto.

In practice, several problems must be dealt with in order to adapt the basic circuit of FIG. 1 so as to provide it with the desired low current drain, highly stable operation that is desired. For example, all OTA devices have some minimum amount of offset, meaning that the output does not switch precisely at the point when the voltage differential across the input terminals is zero, but when the differential is offset by some small amount, generally a fraction of a mV. The offset in the amplifier stage is, of course, amplified such that it has an amplified effect at the input to the second stage comparator OTA. Additionally, the circuitry providing the bias, or reference voltage is, generally speaking, subject to variations as a function of component tolerances and temperature changes, which must also be accounted for. Also, as is evident from FIG. 1, a single amplifier path using two OTAs is not capable of providing a predetermined output signal in response to either negative or positive going input signals. These and other problems are anticipated and dealt with in the various embodiments which are described in the following portion of the specification. For example, in some of the circuit embodiments, the bias voltage is supplied as the out-of-balance voltage of a resistance bridge, the input voltage driving the bridge to balance at which time the comparator switches. The advantage of this arrangement is that the overall circuit is relatively insensitive to variations of the supply source. However, the disadvantage is that adjustment of the bridge has to be relatively accurate, in order to provide for the desired threshold, or sensitivity.

In the discussion to follow, the term sensitivity is employed synonymously with threshold, and refers to the signal level at which the amplifier circuit of this invention provides a change at its output. The output OTA operates with a class A push-pull output characteristic, such that its output current is positive or negative as a function of the level of the input relative to the bias voltage on the reference terminal. However, the gain of the OTAs is sufficiently high that the output current is either an "on" or "off" current for purposes of driving the CMOS transistor element connected to the output of the comparator device. Thus, when used to drive a high input load as in this example, the amplifier circuit provides either an on or off output, with switching occurring at the established sensitivity, or threshold level. It is to be noted, of course, that the amplifier may also be used for linear operations, where the waveform of the output signal is substantially preserved instead of being converted to an on-off level signal, provided the input signal is in excess of the established threshold. Of course, by placing the threshold at zero, the amplifier may be used in an entirely linear operational manner.

Figure 2:
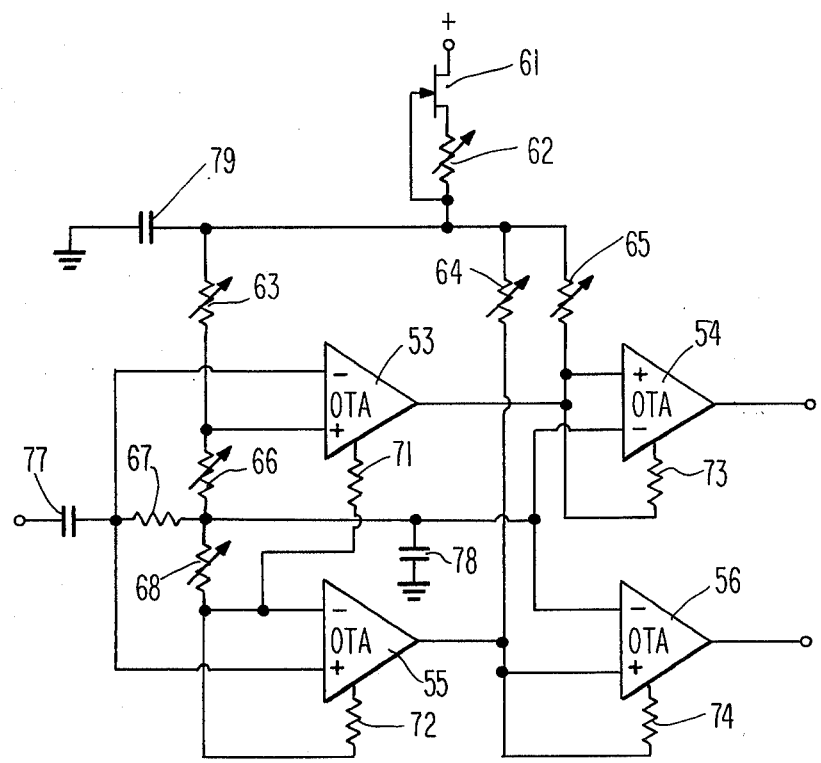
FIG. 2 is a circuit diagram showing a first embodiment of the amplifier circuit of this invention utilizing four OTAs and a single FET current source.

Referring now to FIG. 2, there is shown a circuit diagram of a four OTA embodiment of the amplifier of this invention. A single current source is provided by connection of an FET 61 with a resistor 62 to a positive power source. The output of the current source is connected to resistors 63, 64 and 65 respectively, which are selected to provide the desired division of current. By adjustment of resistors 62, 63, 64 and 65, there are effectively three current sources provided for operation of this circuit. The junction of resistors 63, 64 and 65 is also connected through capacitor 79 to ground.

In this embodiment, there are two paths utilized, comprising amplifier OTA 53 and comparator OTA 54, and amplifier 55 and comparator 56. The input signal is coupled through capacitor 77 to the negative, or inverting terminal of OTA 53 and to the positive, or non-inverting terminal of 55. Current limiting resistor 63 is connected to the positive terminal of OTA 53, and through resistors 66 and 68 to the negative terminal of OTA 55. The negative terminal of OTA 55 is also connected through resistor 71 to the current bias input terminal of OTA 53 and through resistor 72 to the current bias input terminal of OTA 55. Resistor 67 is connected between capacitor 77 and the junction of resistors 66 and 68, which junction is also connected to the two negative, or reference terminals of comparators 54 and 56. Capacitor 78 is connected between such junction and the ground. Resistor 64 is connected to the output of OTA 55, the positive input of OTA 56, and through bias current resistor 74 to the bias input terminal of OTA 56. Resistor 65 is connected to the output of OTA 53, to the positive input terminal of OTA 54, and through resistor 73 to the bias current input terminal of OTA 54. Note that, with this arrangement, each amplifier OTA is loaded with a current source, an OTA input and a bias current resistor in parallel, and the input circuit of each of the four OTAs is driven with a current source.

While this configuration, as shown in FIG. 2, embodies a single FET current source, it is to be understood that an equivalent circuit can comprise three separate current sources, each comprising an FET/resistor combination, whereby high value resistors 63, 64 and 65 can be avoided. In a plural current source configuration, the tolerance of the resistors is not as critical as compared to the one FET arrangement shown in FIG. 2, but two additional FETs are required which can contribute to increased sensitivity drift.

Some of the more specific and detailed advantages of the circuit of FIG. 2 can be understood by a further analysis of the problems associated with sensitivity drift. Assuming a bias voltage on the output OTAs of 200 mV, and a typical gain of the first amplifier OTAs of 16, the input differential voltage to each amplifier stage must be 12.5 mV in order to cause switching at the output. Examining OTA 53, the input consists of the quiescent voltage over resistors 66 and 67, plus the negative going amplitude of the input signal. For negative sensitivity of 2 mV, the voltage over resistor 66 and 67 has to be 10.5 mV. This can be established by adjustment of resistor 66 so that its value, for the given current source, contributes the required quiescent voltage at the input. Likewise, a similar analysis pertains for OTA 55, where the positive sensitivity can be established by adjustment of the value of resistor 68. The adjustments of resistors 66 and 68 do not influence each other, due to the constant current source and the fact that resistors 66 and 68 are small in comparison with resistors 71 and 72. The circuit has a very large adjustment range, relatively independent of the election of the circuit components, and can always be adjusted to a sensitivity of 1 to 2 mV.

However, it is to be noted that the FET current source has a drift with temperature. While a pacer which is implanted in a human patient is maintained at a substantially constant temperature, it is recognized that the adjustment procedure on any circuit would normally be done at room temperature, or about 22° C, following which it would be utilized at the patient temperature of about 37°. The sensitivity drift which accompanies such a 15° change is defined as the 15° drift, or more briefly simply the drift. An FET has a relatively large spread in $V_P$, which is the voltage needed to cut off current flow through the device. Typically, this lies between 300 mV and 1,000 mV, with a temperature drift of 2.2 mV per degree centigrade. If the temperature rises 15° C, the current source experiences an increase of 5% in current for a typical $v_P$ of roughly 650 mV. The temperature drift of FET 61 thus causes approximately a 5% drift of voltage over resistors 66 and 68, which typically would result in a drift of about 0.53 mV. It is to be noted that, for configurations utilizing 3 FETs instead of 1, the difference of $V_P$ between the FETs would introduce additional drift. In any event, it is to be observed that by lowering the voltage across resistors 66 and 68, the amount of drift can be lowered correspondingly. This can be achieved by choosing a lower value for the bias voltage at the comparator OTAs, which is done by adjusting resistors 64 and 65, resulting in a lower adjusted voltage over resistors 66 and 68 and a consequent lower magnitude of drift caused by variations in FET 61. If three FETS are used, bias voltage at the comparator cannot be reduced too much, and for each value of the spread of $V_P$ for a given FET there is an optimal value for the comparator bias voltage. The value of 200 mV, as noted above, corresponds roughly with the spread which has been found in practice.

Figure 3:
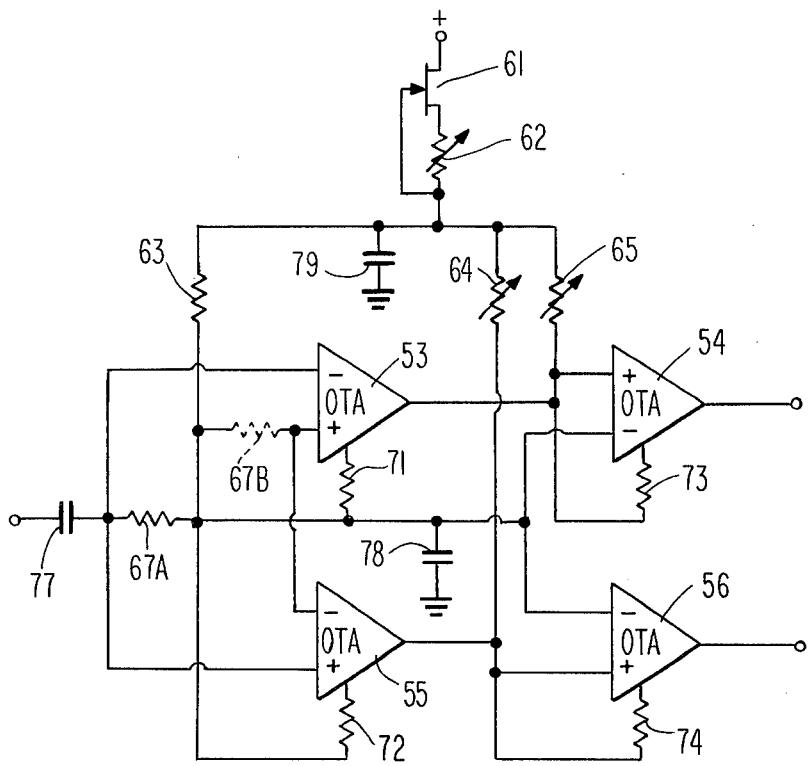
FIG. 3 is a circuit diagram of a second embodiment of the amplifier circuit of this invention, which provides for adjustment of sensitivity through adjustment of the bias voltage on the two output OTAs.

If one FET is used, it is possible to reduce the bias voltage to the point corresponding with resistors 66 and 68 both being equal to 0, as shown in FIG. 3. In this case, the sensitivity is established by adjustment of the resistors 64 and 65. When these resistors are adjusted to provide the desired negative and positive sensitivity, all offsets of the OTAs are also compensated for. In this circuit, the only change caused by temperature drift of the voltage in the input circuit is the voltage across resistor 67A, which corresponds to resistor 67 in FIG. 2. This change in voltage is secondary and not as great as the change across resistors 66 and 68 of FIG. 2, and therefore the resulting sensitivity drift is much lower. For this circuit, the 15° drift is 0.1 to 0.3 mV, with a current drain of about 1.2 uA. By comparison, the typical drift of the circuit of FIG. 2 is about 0.5 mV with a rather high spread. Additional offset compensation can be obtained by including the resistor 67B connected to the positive input terminal of OTA 53 and to the negative input of OTA 55, as shown. With this offset compensation, sensitivity drift is reduced to 0.1 mV or less. It is to be noted that resistor 67A could be decreased in resistance in order to further reduce sensitivity drift, but this change would also reduce the input impedance and thus adversely affect overall gain.

Figure 4:
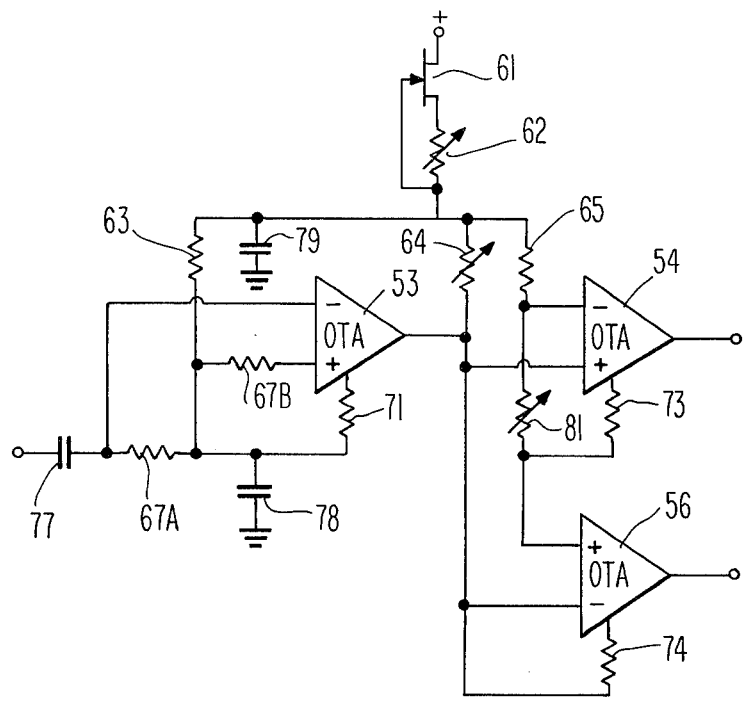
FIG. 4 is a circuit diagram of a third embodiment of the amplifier circuit of this invention, which utilizes one amplifier OTA and two comparator OTAs, and having a bridge circuit adapted for adjustment of the overall circuit sensitivity and driven by a current source

Referring now to FIG. 4, there is shown a circuit diagram of a configuration of the amplifier circuit of this invention utilizing only three OTA units, instead of four as in the previously discussed configurations. It is to be noted that in the configurations where there are two OTA amplifiers, they both receive the same input signal, although they are received with opposite phases. For example, in FIG. 2, two amplifiers must be used because their inputs must be given a different DC-shift. However, the phase inversion required for the purpose of handling both negative going and positive going signals can be accomplished at the second, or comparator stage, while utilizing only one OTA at the amplifier level. This is what is done in FIG. 4, where there is a single amplifier OTA 53, and two comparator amplifiers 54 and 56. The output of OTA 53 is connected to the positive, or non-inverting input terminal of OTA 54, and to the negative, or inverting terminal of OTA 56. By this technique, and by establishing the desired bias voltages on the comparator OTAs 54 and 56, the desired negative and positive sensitivities are obtained.

In the configuration of FIG. 4, the current source is again obtained by an FET 61 and resistor 62, which is connected to a common junction with resistors 63, 64 and 65. Resistor 63 is connected to the positive input of OTA 53, resistor 64 is connected to the output of OTA 53, and resistor 65 is connected to the negative, or reference input terminal of OTA 54 and through adjustable resistor 81 to the positive reference terminal OTA 56. The other circuit components are similar to and serve the same purposes as those in prior configurations. The adjustment of the precise desired sensitivity involves setting resistance 64, which balances a bridge comprised of resistances 64, 65, 73 and 74. In addition, adjustment of resistor 81 enables adjusting of the positive and negative sensitivity. The first stage offset may be compensated by resistor 67B, and any second stage offset is taken into account in the adjustment of resistors 64 and 81. In this configuration, the 15° drift has been measured to be less than 0.5mV; the current drain is 0.9 uA; and, of course, only three OTAs are utilized instead of four.

In the configurations discussed thus far, resistive bridges are employed which are set to be out of balance, thereby normally providing the desired bias voltage. When the amplified input signal drives these bridges to the balance point, the input at one of the comparator OTA devices changes polarity, thereby producing the desired switching signal. Once adjustment of the bridge is achieved, the desired sensitivity is achieved with very low sensitivity drift, and with substantial independence of supply voltage. By contrast, the following circuits do not use a bridge principle, but have a sensitivity which is determined by the tolerance of the resistors utilized. Resistances in the range of about 10 megohms are available with a tolerance of about 10%, which allows for designing the overall circuit characteristics with a tolerance better than most circuits presently available in the art. Furthermore, the stability of the circuit embodiments which follow is sufficiently good that with adjustment an accuracy of only a few percent is easily achieved over a temperature range from 20° to 37° C.

The bridge circuits have a 15° drift which is in principle independent of the adjusted sensitivity. The non-bridge circuits have a 15° drift which is in principle a fixed fraction of the adjusted sensitivity. The drifts mentioned herein for these latter circuits correspond to a sensitivity of 2 mV.

Figure 5:
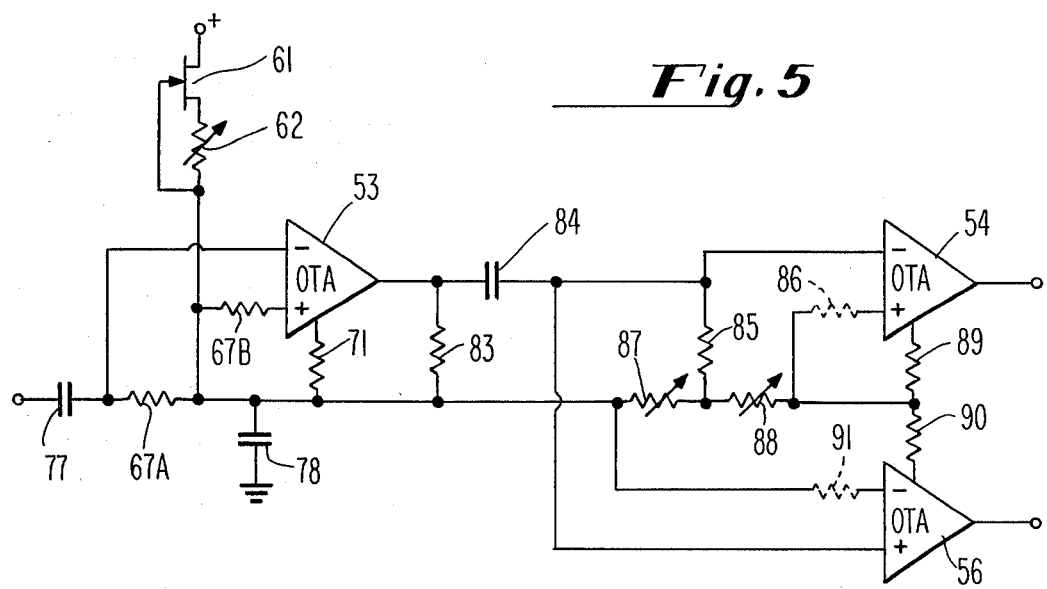
FIG. 5 is a modification of the three OTA embodiment of FIG. 4, with circuitry for establishing the overall sensitivity with a decreased adjustment requirement.

Referring to FIG. 5, there is shown a first example of a configuration of the amplifier circuit of this invention which provides a 15° drift characteristic in the range of 0.1 mV to 0.25 mV. The input signal is connected through capacitor 77 to the negative, or inverting terminal of OTA 53. Capacitor 77 is connected through resistance 67A to the current source comprised of FET 61 and resistor 62, which point is also connected through resistor 67B to the positive input terminal. The output of the current source is also connected to the negative terminal of comparator OTA 56, and through resistors 87 and 88 to the positive terminal of OTA 54. Resistors 86 and 91 may also be connected as shown to the respective input terminals of the comparator OTAs, to reduce the drift. The output of amplifier OTA 53 is connected through capacitor 84 to the negative terminal of OTA 54, and to the positive terminal of OTA 56. Resistor 83 is connected between the output of OTA 53 and the output of the current source. Since the offset voltage of OTA 53 is amplified by the OTA itself, this voltage is blocked by capacitor 84, to avoid the influence of this amplification on the sensitivity. Resistor 83 is needed only to allow capacitor 84 to discharge or charge to the desired DC value. This resistor must be as high as possible in order to minimize its effect on voltage gain.

The tolerance of the sensitivity, without any adjustment of the circuit resistors, is determined by the relative tolerance of resistors 87, 88, 89, 90, 71 and 85. The 15° drift without resistors 86 and 91 has been measured to be 0.1 mV. The current drain with resistor 71 set at 10 Megohm is 0.9 uA, and with resistor 71 set at 5 Megohm, 1.2 uA. In this arrangement, if resistors 87 and 88 are adjusted to obtain the desired sensitivity, resistor 83 and capacitor 75 are superfluous.

Figure 6:
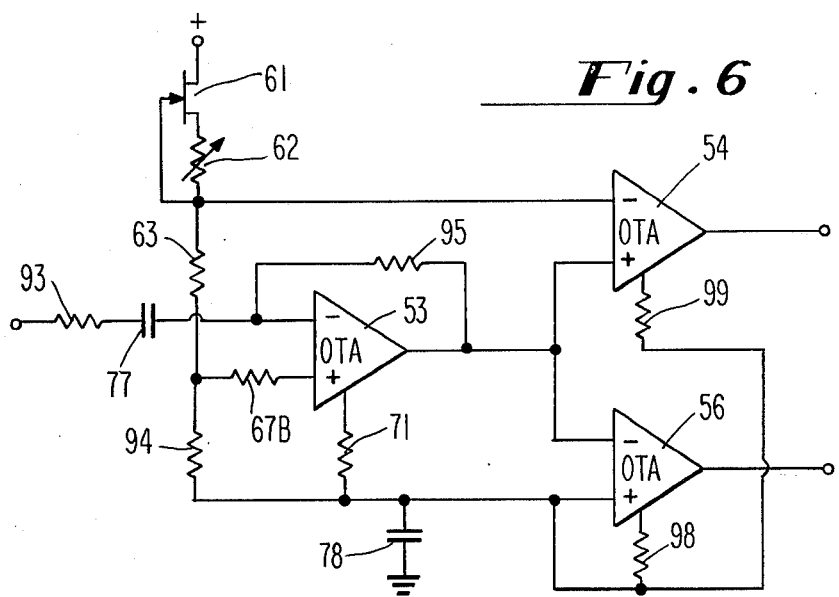
FIG. 6 is another embodiment of the amplifier circuit of this invention utilizing a single OTA amplifier stage and inverting and non-inventing OTA comparator stages driven by the amplifier stage, with a feedback path in the amplifier stage to reduce the effect of first stage offset, thereby reducing the criticality of the sensitivity adjustment and the degree of sensitivity drift.

Referring now to FIG. 6, there is shown a modified circuit designed to provide the optimum accuracy of senitivity without need for adjustment. In this circuit, the output of amplifier OTA 53 is connected through resistor 95 to the negative input terminal, the DC component of the output voltage being completely fed back due to the blocking effect of capacitor 77. As a consequence, the offset voltage of OTA 53 is not amplified. Further, the load which appears across the output of OTA 53 is extremely high, being determined by resistor 95 which is suitably 20 Meg and the inputs of OTAs 54 and 56, which are each typically about 40 Meg. The sensitivity drift is primarily determined by the relative tolerances of resistors 67B and 95, a relative tolerance of 10% causing a 15° drift of less than 0.05 mV. The current drain of this circuit is 0.9 uA for resistor 71 at 10 Meg, and 1.15 M for resistor 71 at 6 Meg.

Figure 7:
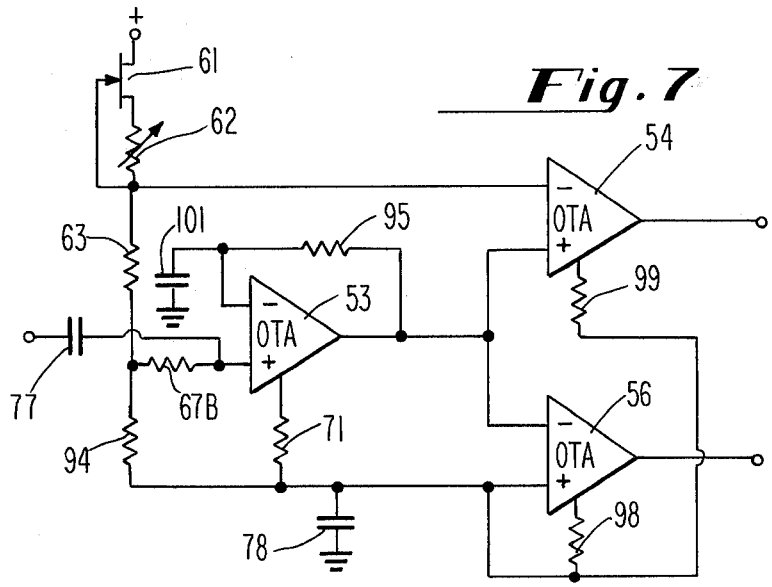
FIG. 7 is a modification of the feedback circuit of FIG. 6, with an altered first stage feedback arrangement which provides higher gain operation.

The circuit configuration as shown in FIG. 7 is varied from that shown in FIG. 6 in that the input is coupled directly through capacitor 77 to the positive input terminal of OTA 53, while the feedback path from the output of OTA 53 is through resistor 95 to the negative terminal. The negative terminal is capacitively connected to ground by capacitor 101. Note that the amplifier of FIG. 7 has no AC-feedback and therefore a higher gain than that of FIG. 6. As a result of driving the positive input instead of the negative input, the amplifier of FIG. 7 also has a higher input resistance.

I claim:

1. An amplifier circuit, comprising:
   a. first and second amplifying paths, each of said paths having first and second input terminals and comprising respective amplifier means for producing a current output as a function of a differential input connected thereto each of said paths containing at least one amplifier element characterized by having a controllable current drain;

b. signal input means for connecting an input signal to respective first input terminals of said paths so as to drive said inputs oppositely;

c. current source means containing a power source, for providing a predetermined source of current; and d. sensitivity means, including a resistive network connected between said current source means and said first and second paths, for controlling both the signal sensitivity of said first and second paths respectively and the current drain of each respective amplifier element.

2. The amplifier circuit as described in claim 1, wherein said sensitivity means connects said current source means with said second input terminals.

3. The circuit as described in claim 1, wherein said sensitivity means comprises a resistive circuit containing at least two resistors having respective resistances of predetermined values and each connected respectively to one of said paths so as to cooperate with said current source in establishing the sensitivity of said amplifying paths.

4. The circuit as described in claim 1, where each of said paths contains first and second operational transconductance amplifiers, with the output of each of said first operational transconductance amplifier directly coupled to an input terminal of each second operational transconductance amplifier, and wherein said sensitivity means combines with said current source means to control the bias current of each operational transconductance amplifier to a predetermined value.

5. The amplifier circuit as described in claim 4, wherein said sensitivity means comprises a bridge circuit connecting said current source and said second operational transconductance amplifiers.

6. The amplifier circuit as described in claim 5, wherein said second operational transconductance amplifiers each have second input terminals, and said sensitivity means is connected to establish a predetermined quiescent voltage across the input terminals of each said second amplifier.

7. The amplifier circuit as described in claim 4, wherein said sensitivity means comprises bias input means connected to said second amplifiers for establishing bias voltages on respective input terminals of said second operational transconductance amplifiers.

8. The amplifier circuit as described in claim 4 wherein said sensitivity means cooperates with said second operational transconductance amplifiers so as to constitute comparator circuits.

9. The amplifier circuit as described in claim 8, comprising offset compensation means for compensating the offset of said first operational transconductance amplifiers, said compensation means being connected between said input means and said second input terminals.

10. An amplifier circuit, comprising:

a. at least one amplifier path comprising first and second OTAs with the output of said first OTA direct coupled to a first input terminal of said second OTA;

b. signal input means for connecting an input signal to a first input of said first OTA;

c. a current circuit for providing a predetermined source of current;

d. connecting means for connecting said current circuit to said amplifier path and the current bias terminal of said second OTA to said first OTA, whereby said first and second OTAs are current controlled; and e. a high impedance active device, the input of said active device being direct connected to the output of said second OTA.

11. The amplifier circuit as described in claim 10, wherein said OTAs have second input terminals, and said connecting means connects to the second input terminal of said first OTA and to the first and second input terminals of said second OTA so as to operate said amplifier path as a comparator which switches its output at a predetermined input delivered by said signal input means.

12. The amplifier circuit as described in claim 11 wherein said connecting means comprises a resistive bridge circuit.

13. The amplifier circuit as described in claim 12, comprising a second amplifier path having first and second OTAs with the output of the first OTA direct coupled to a first input terminal of the second OTA, and wherein said signal input means connects to said first OTA of said one path in an inverting mode and to said first OTA of said second path in a non-inverting mode.

14. The amplifier circuit as described in claim 10, comprising a first resistance network connecting the current bias terminal and said input terminal of said first OTA, with said current circuit.

15. An amplifier circuit, comprising:

a. an amplifier path having at least one active device, and having an input for receiving an input signal and an output for providing an amplified signal, said at least one active device having a current control input terminal;

b. a comparator stage, having an active device with a current control input terminal, said active device having an input terminal being direct coupled to said amplifier path output;

c. current source means for providing a predetermined current to said amplifier path active device current control input terminal; and d. connecting means for connecting said comparator stage active device current control input terminal with said amplifier path.

* * * * *

UNITED STATES PATENT AND TRADEMARK OFFICE
CERTIFICATE OF CORRECTION

PATENT NO. : 4,023,046
DATED : May 10, 1977
INVENTOR(S) : Alexis C. M. Renirie

It is certified that error appears in the above-identified patent and that said Letters Patent are hereby corrected as shown below:

Column 7, line 35, delete "0.5 mV" and insert therefor --0.05 mV--.

Column 8, line 27, after "to be", insert --0.25 mV; and the drift with resistors 86 and 91 has been measured to be--.

Column 10, line 39, after "said", first occurrence, insert --first--.

Signed and Sealed this thirtieth Day of August 1977

[SEAL]

Attest:

RUTH C. MASON
Attesting Officer

C. MARSHALL DANN
Commissioner of Patents and Trademarks